United States Patent
Cahoon et al.

(10) Patent No.: US 6,864,077 B1
(45) Date of Patent: Mar. 8, 2005

(54) MEMBRANE-BOUND DESATURASES

(76) Inventors: Edgar B. Cahoon, 2331 W. 18th St., Wilmington, DE (US) 19806; Rebecca E. Cahoon, 2331 W. 18th St., Wilmington, DE (US) 19806; William D. Hitz, 404 Hillside Rd., Wilmington, DE (US) 19807; Anthony J. Kinney, 609 Lore Ave., Wilmington, DE (US) 19809

( * ) Notice: Subject to any disclaimer, the term of this patent is extended or adjusted under 35 U.S.C. 154(b) by 0 days.

(21) Appl. No.: 09/857,524

(22) PCT Filed: Dec. 2, 1999

(86) PCT No.: PCT/US99/28589

§ 371 (c)(1),
(2), (4) Date: Jun. 4, 2001

(87) PCT Pub. No.: WO00/32790

PCT Pub. Date: Jun. 8, 2000

Related U.S. Application Data

(60) Provisional application No. 60/110,784, filed on Dec. 3, 1998.

(51) Int. Cl.⁷ .......................... C12P 21/06; C12N 9/08; C12N 1/12; C12N 5/00; C07H 21/04
(52) U.S. Cl. ...................... 435/192; 435/69.1; 435/183; 435/189; 435/190; 435/191; 435/252.3; 435/254.2; 435/348; 435/410; 435/415; 435/419; 435/426; 435/320.1; 435/325; 536/23.2; 536/23.4; 536/23.6
(58) Field of Search .................. 435/4, 6.19, 69.1, 435/183, 189, 252.3, 320.1, 325, 348, 410, 415, 419, 426; 536/23.2, 23.5, 23.6, 23.7

(56) References Cited

FOREIGN PATENT DOCUMENTS

| WO | 96/21022 A2 | 7/1996 |
|---|---|---|
| WO | 98/45461 A1 | 10/1998 |

OTHER PUBLICATIONS

Olga Sayanova et al., PNAS, vol. 94:4211–4216, 1997, Expression of a borage desaturase cDNA containing an N–terminal cytochrome b5 domain results in the accumulation of high levels of Delta6–desaturated fatty acids in transgenic tobacco.

Petra Sperling et al, J. Biol. Chem., vol. 273(44):28590–28596, 1998, A Sphingolipid desaturase from higher plants.

EMBL Sequence Listing Database accession No: O82348, Nov. 1, 1998, S. D. Rounsley et al., Arabidopsis thaliana chromosome II BAC T3F17 genomic sequence.

EMBL Sequence Listing Database Accession No: AF031194, Jan. 6, 1999, E. Delhaize et al, Aluminum tolerance in yeast conferred by over–expression of wheat genes.

EMBL Sequence Listing Database Accession No: Q9ZTU8, May 1, 1999, E. Delhaize et al, Aluminum tolerance in yeast conferred by over–expression of wheat genes.

Wen G. Jiang et al., Criti. Rev. in Onco./Hema., vol. 27:179–209, 1998, Essential fatty acids: molecular and cellular basis of their anti–cancer action and clinical implications.

Marlene C. Kruger et al., prog. Lipid Res., vol. 36(2/3):131–151, 1997, Calcium metabolism, osteoporosis and essential fatty acids: a review.

National Center For Biotechnology Information General Identifier No. 2062403, May 2, 1997, O. Sayanova et al., Expression of a borage desaturase cDNA containing an N–terminal cytochrome b5 domain results in the accumulation of high levels of Delta6–desaturated fatty acids in transgenic tobacco.

National Center For Biotechnology Information General Identifier No. 4104056. Jan. 29, 1999. E. Delhaize et al., Aluminum tolerance in yeast conferred by over–expression of wheat genes.

National Center For Biotechnology Information General Identifier No. 1040729, Feb. 3, 2001, P. Sperling et al., A cyctochrome–b5–containing fusion protein similar to plant acyl lipid desaturase.

P. Sperling et al., Biochem. Soc. Trans., vol. 28(6):638–641, 2000, Further characterization of Delta8–sphingollpid desaturases from higher plants.

P. Sperling et al., Eur. J. Biochem., vol. 232(3):798–805, 1995, A cytochrome–b5–containing fusion protein similar to plant acyl lipid desaturase.

Primary Examiner—Manjunath Rao
(74) Attorney, Agent, or Firm—Morgan & Finnegan, L.L.P.

(57) ABSTRACT

This invention relates to an isolated nucleic acid fragment encoding a delta-6 desaturase or sphingolipid desaturase. The invention also relates to the construction of a chimeric gene encoding all or a portion of the delta-6 desaturase or sphingolipid desaturase, in sense or antisense orientation, wherein expression of the chimeric gene results in production of altered levels of the delta-6 desaturase or sphingolipid desaturase in a transformed host cell.

17 Claims, 3 Drawing Sheets

FIGURE 1A

```
bitterbush_[SIN_2]        MEEPK----------------------KHISQADLAKHKQPGDLWISIKGKVYDISKW
soybean_[SIN_8]           M--------------EVVEKEK-----KYITSEELKGHNKEGDLWISIQGKVYNVSDW
borage_[gi_2062403]       MA-------A-----------QIK---KYITSDELKNHDKPGDLWISIQGKAYDVSDW
corn_[SIN_4]              MP--------PSVDAMPAPGDAAGAGDVRMISSKELRAHASADDLWISISGDVYDVTPW
wheat_[SIN_10]            MARTGLADATAPEADAMPAASK--DAADVRMISTKELQAHAAADDLWISISGDVYDVTPW
wheat_[gi_4104056]        MARTGLADATAPEADAMPAASK--DAADVRMISTKELQAHAAADDLWISISGDVYDVTPW
soybean_[SIN_6]           LP-------A-------------------------------------------------
sunflower_[gi_1040729]    MV------SPSIEVLNSIADGK-----KYITSKELKKHNNPNDLWISILGKVYNVTEW bitterbush_[SIN_2]        TKEHPGGELPLLSFAGQDVTDAFIAYHPGTAWQYLDRFFTGYYVQDYSVSEMSKDYRRLV
soybean_[SIN_8]           VKEHPGGDVPISNLAGQDVTDAFIAYHPGTAWSHLEKFFTGYHLSDFKVSEVSKDYRKLA
borage_[gi_2062403]       VKDHPGGSFPLKSLAGQEVTDAFVAFHPASTWKNLDKFFTGYYLKDYSVSEVSKDYRKLV
corn_[SIN_4]              LPHHPGGDLPLLTLAGQDATDAFAAYHPPSARPLLRRFFVG-RLSDYAVSPASADYRRLL
wheat_[SIN_10]            LRHHPGGEVPLITLAGQDATDAFMAYHPPSVRPLLRRFFVG-RLSDYTVPPASADFRRLL
wheat_[gi_4104056]        LRHHPGGEVPLITLAGQDATDAFMAYHPPSVRPLLRRFFVG-RLTDYTVPPASADFRRLL
soybean_[SIN_6]           --------------------------FSTSHRLSDHTVSAASSDYRKLF
sunflower_[gi_1040729]    AKEHPGGDAPLINLAGQDVTDAFIAFHPGTAWKHLDKLFTGYHLKDYQVSDISRDYRKLA bitterbush_[SIN_2]        SEFSKMGLFKTPGKGVYCSIFFVSVLFALSVYGVLYCKSTWAHLCSGLLMGMLWLQSGWV
soybean_[SIN_8]           SEFSKLGLFDTKGHVTSCTLASVAVMFLIVLYGVLRCTSVWAHLGSGMLLGLLWMQSAYV
borage_[gi_2062403]       FEFSKMGLYDKKGHIMFATLCFIAMLFAMSVYGVLFCEGVLVHLFSGCLMGFLWIQSGWI
corn_[SIN_4]              AQLSSAGLFERVGPTPKVQLVLMAVLFYAALYLVLACASAWAHLLAGGLIGFVWIQSGWM
wheat_[SIN_10]            AQLSSAGLFERVGHTPKFLLVAMSVLFCIALYCVLACSSTGAHMFAGGLIGFIWIQSGWI
wheat_[gi_4104056]        AQLSSAGLFERVGHTPKFLLVAMSVLFCIALYCVLACSSTGAHMFAGGLIGFIWIQSGWI
soybean_[SIN_6]           SDLSALNLFNRKGHTTSILLSLILTLFLPLSVCGVLFSDSTFVHVLSAALIGFLWIQSGWI
sunflower_[gi_1040729]    SEFAKAGMFEKKGHGVIYSLCFVSLLLSACVYGVLYSGSFWIHMLSGAILGLAWMQIAYL
```

FIGURE 1B

```
bitterbush_[SIN_2]         GHDSCHYQVMPNRKLNRLFQIIAGNVIAGVSVAWWKLDHNTHHFACNSANLDPDIQHLPI
soybean_[SIN_8]            GHDSGHYVVMTTNGFNKVAQILSGNCLTGISIAWWKWTHNAHHIACNSLDHDPDLQHMPV
borage_[gi_2062403]        GHDAGHYMVSDSRLNKFMGIFAANCLSGISIGWWKWNHNAHHIACNSLEYDPDLQYIPF
corn_[SIN_4]               GHDSGHHRITGHPVLDRVVQVLSGNCLTGLSIAWWKCNHNTHHIACNSLDHDPDLQHMPL
wheat_[SIN_10]             GHDSGHHQITRHPALNRLLQVVSGNCLTGLGIAWWKFNHNTHHISCNSLDHDPDLQHLPL
wheat_[gi_4104056]         GHDSGHHQITRHPALNRLLQVVSGNCLTGLGIAWWKFNHNTHHISCNSLDHDPDLQHLPL
soybean_[SIN_6]            GHDSGHYNVMLSRRLNRAIQILSGNILAGISIGWWKWNHNAHHIACNSLDYDPDLQHMPV
sunflower_[gi_1040729]     GHDAGHYQMATRGWNKFAGIFIGNCITGISIAWWKWTHNAHHIACNSLDYDPDLQHLPM bitterbush_[SIN_2]         IAISPKFFNSLTSYYHNCKMTYDRAARFFVSFQHWTFYPALLSVRLYLFILSFKVVFSNN
soybean_[SIN_8]            FAVSSRFFNSITSHFYGRKLEFDFIARFLICYQHFTFYPVMCVARVNLYLQTILLLFSR-
borage_[gi_2062403]        LVVSSKFFGSLTSHFYEKRLTFDSLSRFFVSYQHWTFYPIMCAARLNMYVQSLIMLLTK-
corn_[SIN_4]               FAVSPKLFGNIWSYFYQRTLAFDAASKFFISYQHWTFYPVMCIARINLLAQSALFVLTE-
wheat_[SIN_10]             FAVSTKLFNNLWSVCYERTLAFDAISKFFVSYQHWTFYPVMGFARINLLVQSIVFLITQ-
wheat_[gi_4104056]         FAVSTKLFNNLWSVCYERTLAFDAISKFFVSYQHWTFYPVMGFARINLLVQSIVFLITQ-
soybean_[SIN_6]            FAVSSRFFNSITSHXYGRKXEFDXIAXFLICYQHFTFYPVMCVARVNLYLQTILLLFSR-
sunflower_[gi_1040729]     LAVSSKLFNSITSVFYGRQLTFDPLARFFVSYQHYLYYPIMCVARVNLYLQTILLLISKbitterbush_[SIN_2]         KRVYKRSQEILGYAAFLTWYSLLLSRLPNWPERVMYFTSCLAVAGFQHWQFSLNHFASNV
soybean_[SIN_8]            RKVQDRALNIMGILVFWTWFPLLVSCLPNWPERVMFVLASFAVCSIQHIQFCLNHFAANV
borage_[gi_2062403]        RNVSYRAHELLGCLVFSIWYPLLVSCLPNWGERIMFVIASLSVTGMQQVQFSLNHFSSSV
corn_[SIN_4]               KRVPQRLLEIAGVATFWANYPLLVASLPNWWERVAFVLFSFTICGIQHVQFCLNHFSSDV
wheat_[SIN_10]             KKVRQRWLEIAGVAAFVWNYPLLVSCLPNWWERVAFVLASFVITGIQHVQFCLNHFSSAV
wheat_[gi_4104056]         KKVRQRWLEIAGVAAFVWVYPLLVSCLPNWWERVAFVLASFVITGIQHVQFCLNHFSSAV
soybean_[SIN_6]            XKVQDRALNIMGILVFWTWFLFLLA------LLFV-----PIQHIQFWLNHLAENL
sunflower_[gi_1040729]     RKIPDRGLNILGTLIFWTWFPLLVSRLPNWPERVAFVLVSFCVTGIQHIQFTLNHFSGDV
```

FIGURE 1C

```
bitterbush_[SIN_2]          YTGLPSGNDWFHQQTKGTLNITASAWWDWFHGGLHFQIEHHLFPRMPKCHFRKISPIVNK
soybean_[SIN_8]             YVGPPSGNDWFEKQTSGTLDISCASSMDWFFGGLQFQLEHHLFPRLPRCQLRKISPLVSD
borage_[gi_2062403]         YVGKPKGNNWFEKQTDGTLDISCPPWMDWFHGGLQFQIEHHLFPKMPRCNLRKISPYVIE
corn_[SIN_4]                YVGPPKGNDWFEKQTAGTLDILCSPWMDWFHGGLQFQIEHHLFPRLPRCHLRKVAPAVRD
wheat_[SIN_10]              YVGPPKGNDWFERQTAGTLDIKCSPWMDWFHGGLQFVEHHLFPRLPRCHYRMVAPIVRD
wheat_[gi_4104056]          YVGPPKGNDWFERQTAGTLDIKCSPWMDWFHGGLQFVEHHLFPRLPRCHYRMVAPIVRD
soybean_[SIN_6]             YXG---------------------------------------------------------
sunflower_[gi_1040729]      YVGPPKGDNWFEKQTRGTIDIACSSWMDWFFGGLQFQLEHHLFPRLPRCHLRSISPICRE bitterbush_[SIN_2]          LCQKHNLSYETATMWEANKMVYSTLRAVAMEAKDVTK-PVPKNMVWEAMNTFG
soybean_[SIN_8]             LCKKHNLPYRSLSFWEANQWTIRTLRTLRTAALQARDLTN-PAPKNLLWEAVNTHG
borage_[gi_2062403]         LCKKHNLPYNYASFSKANEMTLRTLRNTALQARDITK-PLPKNLVWEALHTHG
corn_[SIN_4]                LCKKHGLTYSAATFWGANVLTWKTLRAAALQARTATSGGAPKNLVWEAVNTHG
wheat_[SIN_10]              LCKKHGLSYGAATFWEANVMTWKTLRAAALQAREATTGAAPKNLVWEALNTHG
wheat_[gi_4104056]          LCKKHGLSYGAATFWEANVMTWKTLRAAALQAREATTGAAPKNLVWEALNTHG
soybean_[SIN_6]             -----------------------------------------------------
sunflower_[gi_1040729]      LCKKYNLPYVSLSFYDANVTTLKTLRTAALQARDLTN-PAPQNLAWEAFNTHG
```

SEQUENCE LISTING

```
<160> NUMBER OF SEQ ID NOS: 17

<210> SEQ ID NO 1
<211> LENGTH: 1471
<212> TYPE: DNA
<213> ORGANISM: Picramnia pentandra
<220> FEATURE:
<221> NAME/KEY: unsure
<222> LOCATION: (1402)
<223> OTHER INFORMATION: n = A, C, G, or T

<400> SEQUENCE: 1
cttccttgtt cctggaattt tcaaatcact tcctctgttg cacttcaatg gaagagccaa      60
agaagcacat ttcgcaagca gaccttgcaa agcataagca accaggagat ttatggatct     120
ctatcaaggg aaaagtttac gatatctcca agtggactaa agagcatccc ggtggtgagc     180
tcccattgtt aagttttgcc ggccaagatg tcactgatgc gttcattgct taccatcctg     240
gcactgcttg gcaataacct tgacaggttct ttactgggta ctacgttcaa gattactctg     300
tctctgagat gtccaaggac tacagaaggc tcgtctctga gttttctaag atgggtttgt     360
tcaagacacc aggcaaaggg gtctactgct caatcttttt cgtgtctgtg ttgttcgctc     420
tgagtgttta cggtgttctc tactgcaaga gcacctgggc tcatctttgc tctggtttgc     480
taatgggtat gctatggctc cagagtggtt gggtggggca tgattcttgt cactaccaag     540
ttatgcctaa ccgtaagctt aatcgtcttt ttcaaatcat tgcaggaaat gtgattgctg     600
gtgttagtgt tgcatggtgg aagttggacc ataacaccca tcactttgcc tgtaatagcg     660
ccaatctgga tcctgatatt cagcaccttc ctataattgc catatcccca aaatttttca     720
actcccttac atcatactat cacaactgca aaatgaccta tgatcgcgct gccaggtttt     780
ttgttagctt tcagcactgg acatttatc ctgcattgtt aagcgttagg ctctatcttt     840
ttattctgtc ttttaaggtg gtgttttcca acaacaaaag ggtatacaag agaagtcagg     900
```

```
aaattttagg ctatgcagct ttcttgactt ggtattctct actcctttct cgcctaccca      960
attggcctga aagggtcatg tatttcacgt cctgtttagc agtcgccggg ttccaacatt     1020
ggcagttcag cttgaatcac tttgcttcta atgtttacac tggtttgcct agcggtaatg     1080
attggtttca ccagcagaca aagggcacgc tcaacataac agcttctgct tggtgggatt     1140
ggtttcatgg tggcctgcac tttcagattg agcatcatct gtttccaagg atgcctaagt     1200
gccatttcag gaaaatctca cccattgtga acaaactttg ccagaagcat aatttgtcct     1260
atgaaactgc taccatgtgg gaggccaata aatggtata ctccaccctg cgtgctgtgg      1320
ctatggaagc taaggatgtt accaagccag ttcccaagaa catggtctgg gaagcaatga     1380
acactttcgg gtgaacctta tnaaacatca agtgctgtct ttcccgtaaa agcttccagt     1440
cccaatgttt cttttttttt ttttttttttt t                                   1471
```

<210> SEQ ID NO 2
<211> LENGTH: 448
<212> TYPE: PRT
<213> ORGANISM: Picramnia pentandra

<400> SEQUENCE: 2

```
Met Glu Glu Pro Lys Lys His Ile Ser Gln Ala Asp Leu Ala Lys His
  1               5                  10                  15

Lys Gln Pro Gly Asp Leu Trp Ile Ser Ile Lys Gly Lys Val Tyr Asp
                 20                  25                  30

Ile Ser Lys Trp Thr Lys Glu His Pro Gly Gly Glu Leu Pro Leu Leu
             35                  40                  45

Ser Phe Ala Gly Gln Asp Val Thr Asp Ala Phe Ile Ala Tyr His Pro
         50                  55                  60

Gly Thr Ala Trp Gln Tyr Leu Asp Arg Phe Phe Thr Gly Tyr Tyr Val
     65                  70                  75                  80

Gln Asp Tyr Ser Val Ser Glu Met Ser Lys Asp Tyr Arg Arg Leu Val
                 85                  90                  95

Ser Glu Phe Ser Lys Met Gly Leu Phe Lys Thr Pro Gly Lys Gly Val
                100                 105                 110

Tyr Cys Ser Ile Phe Phe Val Ser Val Leu Phe Ala Leu Ser Val Tyr
            115                 120                 125

Gly Val Leu Tyr Cys Lys Ser Thr Trp Ala His Leu Cys Ser Gly Leu
        130                 135                 140

Leu Met Gly Met Leu Trp Leu Gln Ser Gly Trp Val Gly His Asp Ser
145                 150                 155                 160

Cys His Tyr Gln Val Met Pro Asn Arg Lys Leu Asn Arg Leu Phe Gln
                165                 170                 175

Ile Ile Ala Gly Asn Val Ile Ala Gly Val Ser Val Ala Trp Trp Lys
            180                 185                 190

Leu Asp His Asn Thr His His Phe Ala Cys Asn Ser Ala Asn Leu Asp
        195                 200                 205

Pro Asp Ile Gln His Leu Pro Ile Ile Ala Ile Ser Pro Lys Phe Phe
    210                 215                 220

Asn Ser Leu Thr Ser Tyr Tyr His Asn Cys Lys Met Thr Tyr Asp Arg
225                 230                 235                 240

Ala Ala Arg Phe Phe Val Ser Phe Gln His Trp Thr Phe Tyr Pro Ala
                245                 250                 255

Leu Leu Ser Val Arg Leu Tyr Leu Phe Ile Leu Ser Phe Lys Val Val
            260                 265                 270
```

```
Phe Ser Asn Asn Lys Arg Val Tyr Lys Arg Ser Gln Glu Ile Leu Gly
            275                 280                 285

Tyr Ala Ala Phe Leu Thr Trp Tyr Ser Leu Leu Ser Arg Leu Pro
        290                 295                 300

Asn Trp Pro Glu Arg Val Met Tyr Phe Thr Ser Cys Leu Ala Val Ala
305                 310                 315                 320

Gly Phe Gln His Trp Gln Phe Ser Leu Asn His Phe Ala Ser Asn Val
                325                 330                 335

Tyr Thr Gly Leu Pro Ser Gly Asn Asp Trp Phe His Gln Gln Thr Lys
                340                 345                 350

Gly Thr Leu Asn Ile Thr Ala Ser Ala Trp Trp Asp Trp Phe His Gly
            355                 360                 365

Gly Leu His Phe Gln Ile Glu His His Leu Phe Pro Arg Met Pro Lys
        370                 375                 380

Cys His Phe Arg Lys Ile Ser Pro Ile Val Asn Lys Leu Cys Gln Lys
385                 390                 395                 400

His Asn Leu Ser Tyr Glu Thr Ala Thr Met Trp Glu Ala Asn Lys Met
                405                 410                 415

Val Tyr Ser Thr Leu Arg Ala Val Ala Met Glu Ala Lys Asp Val Thr
                420                 425                 430

Lys Pro Val Pro Lys Asn Met Val Trp Glu Ala Met Asn Thr Phe Gly
            435                 440                 445

<210> SEQ ID NO 3
<211> LENGTH: 1764
<212> TYPE: DNA
<213> ORGANISM: Zea mays

<400> SEQUENCE: 3
gcacgagctc cctctctctc cccaatcctc cccgcctccc cctaccaaat cagcaccacc     60
caaggcgcat ccgagccacg gccgcgcaat gccgccctct gtcgatgcaa tgccggcccc    120
cggcgacgcc gcgggcgccg cgacgtgcg catgatctcc tccaaggagc tccgcgctca    180
cgcttccgcc gacgacctct ggatctccat ctccggcgac gtgtacgacg tcacgccctg    240
gctcccccac cacccgggcg cgacctcc gcttctcacc ctggcggggc aggacgccac    300
cgacgccttc gccgcctacc acccgccctc ggcgcgcccg ctcctccgcc gcttcttcgt    360
tggccgcctc tctgactacg ccgtctcccc cgcgtccgcc gactaccgcc gcctcctcgc    420
gcagctatcc tccgcgggcc tcttcgaacg cgtcggcccc accccaagg tccagctcgt    480 cctgatggcc gtcctcttct acgccgcgct gtacctcgtc ctcgcatgcg ccagcgcctg    540 ggcgcaccte ctcgcggggg gtctcattgg cttcgtctgg atccagtccg ctggatggg    600 ccacgactcg ggccaccacc gcatcaccgg ccatccggtc ctcgaccgcg tcgtgcaggt    660
gctctccggg aactgcctca ccggcctcag catcgcctgg tggaagtgta accacaacac    720
gcaccacatc gcctgcaaca gcctggacca tgacccggac ctccagcaca tgccgctctt    780
tgccgtctcc cccaagctgt tcggcaacat atggtcctac ttctaccaac ggaccctggc    840
gttcgatgcc gcctcgaaat tcttcatcag ctaccagcac tggaccttct acccggtaat    900
gtgcatcgcc aggataaatc ttctcgcgca gtccgccctg ttcgttctca cggagaagag    960
ggtgccgcag cggttgcttg agatcgcggg ggtcgccaca ttctgggctt ggtacccgtt   1020
gctggtggct tccctgccga attggtggga gagggtcgcg tttgtgcttt tcagcttcac   1080
catctgcggg attcagcacg tccaattctg cctgaaccac ttctcgtccg acgtgtatgt   1140
```

-continued

```
cgggccaccc aagggcaatg actggtttga gaagcagacg gcaggcacgc tcgacatcct    1200
gtgctctcct tggatggatt ggttccacgg tggcctgcag ttccagattg agcaccatct    1260
gtttccccgc ctacctcggt gccaccttcg caaggttgca ccggccgtcc gcgacctttg    1320
caagaagcat gggctcactt attctgcagc cacattctgg ggtgcaaatg tgcttacatg    1380
gaagacactc agggctgctg cattgcaggc caggaccgct acaagtggtg gtgctccgaa    1440
gaatttggta tgggaggctg tgaacaccca tggataaatg ggatgaagat acgggctaat    1500
ggcaacttct ggtgttcagc ttggtgccca tgtgattgtc tggatgcctt tcagttattt    1560
agagatattg atcattcaac ctgcctgagt caggttggaa ttttcgtgtt gacaagtggc    1620
tgtctatcca gttggagagt tcatgcttca atagtctggt tgttcacggg atgttctgtt    1680
ctccctatca cggtaactat atgatgatga tccttgcttt aattcatgaa cacttgtttc    1740
aagattaaaa aaaaaaaaaa aaaa                                           1764
```

<210> SEQ ID NO 4
<211> LENGTH: 462
<212> TYPE: PRT
<213> ORGANISM: Zea mays

<400> SEQUENCE: 4

```
Met Pro Pro Ser Val Asp Ala Met Pro Ala Pro Gly Asp Ala Ala Gly
  1               5                  10                  15

Ala Gly Asp Val Arg Met Ile Ser Ser Lys Glu Leu Arg Ala His Ala
             20                  25                  30

Ser Ala Asp Asp Leu Trp Ile Ser Ile Ser Gly Asp Val Tyr Asp Val
         35                  40                  45

Thr Pro Trp Leu Pro His His Pro Gly Gly Asp Leu Pro Leu Leu Thr
     50                  55                  60

Leu Ala Gly Gln Asp Ala Thr Asp Ala Phe Ala Ala Tyr His Pro Pro
 65                  70                  75                  80

Ser Ala Arg Pro Leu Leu Arg Arg Phe Phe Val Gly Arg Leu Ser Asp
                 85                  90                  95

Tyr Ala Val Ser Pro Ala Ser Ala Asp Tyr Arg Arg Leu Leu Ala Gln
            100                 105                 110

Leu Ser Ser Ala Gly Leu Phe Glu Arg Val Gly Pro Thr Pro Lys Val
        115                 120                 125

Gln Leu Val Leu Met Ala Val Leu Phe Tyr Ala Leu Tyr Leu Val
    130                 135                 140

Leu Ala Cys Ala Ser Ala Trp Ala His Leu Leu Ala Gly Gly Leu Ile
145                 150                 155                 160

Gly Phe Val Trp Ile Gln Ser Gly Trp Met Gly His Asp Ser Gly His
                165                 170                 175

His Arg Ile Thr Gly His Pro Val Leu Asp Arg Val Val Gln Val Leu
            180                 185                 190

Ser Gly Asn Cys Leu Thr Gly Leu Ser Ile Ala Trp Trp Lys Cys Asn
        195                 200                 205

His Asn Thr His His Ile Ala Cys Asn Ser Leu Asp His Asp Pro Asp
    210                 215                 220

Leu Gln His Met Pro Leu Phe Ala Val Ser Pro Lys Leu Phe Gly Asn
225                 230                 235                 240

Ile Trp Ser Tyr Phe Tyr Gln Arg Thr Leu Ala Phe Asp Ala Ala Ser
                245                 250                 255
```

-continued

```
Lys Phe Phe Ile Ser Tyr Gln His Trp Thr Phe Tyr Pro Val Met Cys
            260                 265                 270

Ile Ala Arg Ile Asn Leu Leu Ala Gln Ser Ala Leu Phe Val Leu Thr
        275                 280                 285

Glu Lys Arg Val Pro Gln Arg Leu Leu Glu Ile Ala Gly Val Ala Thr
    290                 295                 300

Phe Trp Ala Trp Tyr Pro Leu Leu Val Ala Ser Leu Pro Asn Trp Trp
305                 310                 315                 320

Glu Arg Val Ala Phe Val Leu Phe Ser Phe Thr Ile Cys Gly Ile Gln
                325                 330                 335

His Val Gln Phe Cys Leu Asn His Phe Ser Ser Asp Val Tyr Val Gly
            340                 345                 350

Pro Pro Lys Gly Asn Asp Trp Phe Glu Lys Gln Thr Ala Gly Thr Leu
        355                 360                 365

Asp Ile Leu Cys Ser Pro Trp Met Asp Trp Phe His Gly Gly Leu Gln
370                 375                 380

Phe Gln Ile Glu His His Leu Phe Pro Arg Leu Pro Arg Cys His Leu
385                 390                 395                 400

Arg Lys Val Ala Pro Ala Val Arg Asp Leu Cys Lys Lys His Gly Leu
                405                 410                 415

Thr Tyr Ser Ala Ala Thr Phe Trp Gly Ala Asn Val Leu Thr Trp Lys
            420                 425                 430

Thr Leu Arg Ala Ala Ala Leu Gln Ala Arg Thr Ala Thr Ser Gly Gly
        435                 440                 445

Ala Pro Lys Asn Leu Val Trp Glu Ala Val Asn Thr His Gly
    450                 455                 460

<210> SEQ ID NO 5
<211> LENGTH: 880
<212> TYPE: DNA
<213> ORGANISM: Glycine max
<220> FEATURE:
<221> NAME/KEY: unsure
<222> LOCATION: (496)
<223> OTHER INFORMATION: n = A, C, G, or T
<220> FEATURE:
<221> NAME/KEY: unsure
<222> LOCATION: (512)
<223> OTHER INFORMATION: n = A, C, G, or T
<220> FEATURE:
<221> NAME/KEY: unsure
<222> LOCATION: (523)
<223> OTHER INFORMATION: n = A, C, G, or T
<220> FEATURE:
<221> NAME/KEY: unsure
<222> LOCATION: (532)
<223> OTHER INFORMATION: n = A, C, G, or T
<220> FEATURE:
<221> NAME/KEY: unsure
<222> LOCATION: (630)
<223> OTHER INFORMATION: n = A, C, G, or T
<220> FEATURE:
<221> NAME/KEY: unsure
<222> LOCATION: (700)
<223> OTHER INFORMATION: n = A, C, G, or T
<220> FEATURE:
<221> NAME/KEY: unsure
<222> LOCATION: (730)
<223> OTHER INFORMATION: n = A, C, G, or T
<220> FEATURE:
<221> NAME/KEY: unsure
<222> LOCATION: (738)
<223> OTHER INFORMATION: n = A, C, G, or T
<220> FEATURE:
<221> NAME/KEY: unsure
<222> LOCATION: (761)
```

```
<223> OTHER INFORMATION: n = A, C, G, or T
<220> FEATURE:
<221> NAME/KEY: unsure
<222> LOCATION: (764)
<223> OTHER INFORMATION: n = A, C, G, or T
<220> FEATURE:
<221> NAME/KEY: unsure
<222> LOCATION: (814)
<223> OTHER INFORMATION: n = A, C, G, or T
<220> FEATURE:
<221> NAME/KEY: unsure
<222> LOCATION: (822)
<223> OTHER INFORMATION: n = A, C, G, or T
<220> FEATURE:
<221> NAME/KEY: unsure
<222> LOCATION: (824)
<223> OTHER INFORMATION: n = A, C, G, or T
<220> FEATURE:
<221> NAME/KEY: unsure
<222> LOCATION: (838)
<223> OTHER INFORMATION: n = A, C, G, or T
<220> FEATURE:
<221> NAME/KEY: unsure
<222> LOCATION: (842)
<223> OTHER INFORMATION: n = A, C, G, or T
<220> FEATURE:
<221> NAME/KEY: unsure
<222> LOCATION: (876)
<223> OTHER INFORMATION: n = A, C, G, or T

<400> SEQUENCE: 5
ccgcctccct cctcctcccc gccttctcca cctcccaccg tctttccgac cacaccgtct      60
ccgccgcctc ctccgactac cgcaagctct tctccgacct ctcgcgctc aacctcttca     120 accgcaaggg ccacacaacc tccatcctcc tctcccttat tctcacccctt tttcctctct    180 ctgtctgcgg cgtcctcttc tccgacagca ctttcgtgca cgtgctttcc gctgcattga    240
taggctttct ctggattcag agcggctgga taggccacga ctccggccat tacaacgtga    300
tgctcagccg ccgcctcaac cgcgcaattc agattctctc cggcaacatt ctcgccggaa    360
tcagcatcgg ctggtggaag tggaaccaca acgcccacca cattgcatgc aacagcctcg    420
actatgaccc tgatctgcag cacatgccgg tctttgcagt ttcgtcgcgg ttcttcaatt    480
ccataacctc tcattnctat gggaggaagt tngagtttga ttncattgct angttcttga    540
tctgctacca gcactttact tttttacccgg taatgtgtgt tgccagggtc aacttgtatc    600
tgcagacaat tctgctattg ttttcgaggn gaaaagtgca ggatagagct tgaacataat    660
ggggatcctt tgtttttgga cttggttcct cttttagtgn cttgcctgcc aaattgggcc    720 tgatagggn atgtttgngc ttgctagctt tgctgtttgt nccnatccag cacattcagt     780
tctggttgaa tcaccttgct gaaaatttat atgncgggca cnantgggaa tgactggntg    840
anaatcagac aagggggtcat tggatatctc ttgtgnccct                         880

<210> SEQ ID NO 6
<211> LENGTH: 253
<212> TYPE: PRT
<213> ORGANISM: Glycine max
<220> FEATURE:
<221> NAME/KEY: UNSURE
<222> LOCATION: (161)
<223> OTHER INFORMATION: Xaa = ANY AMINO ACID
<220> FEATURE:
<221> NAME/KEY: UNSURE
<222> LOCATION: (166)
<223> OTHER INFORMATION: Xaa = ANY AMINO ACID
<220> FEATURE:
<221> NAME/KEY: UNSURE
<222> LOCATION: (170)
<223> OTHER INFORMATION: Xaa = ANY AMINO ACID
```

-continued

```
<220> FEATURE:
<221> NAME/KEY: UNSURE
<222> LOCATION: (173)
<223> OTHER INFORMATION: Xaa = ANY AMINO ACID
<220> FEATURE:
<221> NAME/KEY: UNSURE
<222> LOCATION: (206)
<223> OTHER INFORMATION: Xaa = ANY AMINO ACID
<220> FEATURE:
<221> NAME/KEY: UNSURE
<222> LOCATION: (252)
<223> OTHER INFORMATION: Xaa = ANY AMINO ACID

<400> SEQUENCE: 6

Leu Pro Ala Phe Ser Thr Ser His Arg Leu Ser Asp His Thr Val Ser
  1               5                  10                  15

Ala Ala Ser Ser Asp Tyr Arg Lys Leu Phe Ser Asp Leu Ser Ala Leu
             20                  25                  30

Asn Leu Phe Asn Arg Lys Gly His Thr Thr Ser Ile Leu Leu Ser Leu
         35                  40                  45

Ile Leu Thr Leu Phe Pro Leu Ser Val Cys Gly Val Leu Phe Ser Asp
 50                  55                  60

Ser Thr Phe Val His Val Leu Ser Ala Ala Leu Ile Gly Phe Leu Trp
 65                  70                  75                  80

Ile Gln Ser Gly Trp Ile Gly His Asp Ser Gly His Tyr Asn Val Met
             85                  90                  95

Leu Ser Arg Arg Leu Asn Arg Ala Ile Gln Ile Leu Ser Gly Asn Ile
        100                 105                 110

Leu Ala Gly Ile Ser Ile Gly Trp Trp Lys Trp Asn His Asn Ala His
        115                 120                 125

His Ile Ala Cys Asn Ser Leu Asp Tyr Asp Pro Asp Leu Gln His Met
    130                 135                 140

Pro Val Phe Ala Val Ser Ser Arg Phe Phe Asn Ser Ile Thr Ser His
145                 150                 155                 160

Xaa Tyr Gly Arg Lys Xaa Glu Phe Asp Xaa Ile Ala Xaa Phe Leu Ile
                165                 170                 175

Cys Tyr Gln His Phe Thr Phe Tyr Pro Val Met Cys Val Ala Arg Val
            180                 185                 190

Asn Leu Tyr Leu Gln Thr Ile Leu Leu Leu Phe Ser Arg Xaa Lys Val
        195                 200                 205

Gln Asp Arg Ala Leu Asn Ile Met Gly Ile Leu Val Phe Trp Thr Trp
    210                 215                 220

Phe Leu Phe Leu Leu Ala Leu Leu Phe Val Pro Ile Gln His Ile Gln
225                 230                 235                 240

Phe Trp Leu Asn His Leu Ala Glu Asn Leu Tyr Xaa Gly
                245                 250

<210> SEQ ID NO 7
<211> LENGTH: 1934
<212> TYPE: DNA
<213> ORGANISM: Glycine max

<400> SEQUENCE: 7
gcacgagcac acaagtaaaa ccttagagag agagagagag agagagagag ggtaaaaggg      60
tattagatcc ttgaaccaga tcaaatcatc aaaatctctg tctatggggt tgtgaaaaca     120
acaatcacat tgttgttgct gtaaaagggg attccttagt ctagatttgt ttgcattgca     180
gaagaaccag atacccccatt attgttccta tctatctatc tgtctatatt ctatttatct    240
```

-continued

```
tcttattgta gttctcattg tgtctgattt cagtgatttg tgttgttttt ggttaacaca      300
agcaatggag gttgttgaga aggagaagaa gtacataacc tcagaggagc tgaagggtca      360
caacaaggag ggagatttat ggatctcaat tcaaggtaag gtgtacaatg tctcagattg      420
ggtcaaggag caccctggtg gtgatgttcc aatctcaaac cttgctggcc aggatgtcac      480
tgatgcattc atagcatacc atcctggcac agcatggtca caccttgaaa aattcttcac      540
tggctaccac ctcagtgact tcaaggtctc tgaggtgtcc aaagactaca gaaagcttgc      600
atctgagttc tcaaaattgg gtcttttttga caccaaaggg catgtcactt catgcacccct      660
tgcatctgtt gctgttatgt tcctcattgt actctatggt gttctgaggt gcactagtgt      720
gtgggctcat ttgggttcag gcatgctctt agggttgctt tggatgcaaa gtgcttatgt      780
gggccatgat tctggccact atgtggttat gacaaccaat ggtttcaaca aggttgcaca      840
gatcctctct gggaactgct tgaccgggat aagcattgct tggtggaagt ggactcacaa      900
tgctcaccac attgcgtgca acagccttga ccatgaccct gatctgcagc acatgccggt      960
ctttgcagtt tcgtcgcggt tcttcaattc cataacctct catttctatg gaggaagtt      1020
ggagtttgat tcattgcta ggttcttgat ctgctaccag cactttactt tttacccggt      1080
aatgtgtgtt gccagggtca acttgtatct gcagacaatt ctgctattgt tttcgaggcg      1140
aaaagtgcag gatagagcct tgaacataat ggggatcctt gtgttttgga cttggttccc      1200
tcttttagtg tcttgcctgc caaattggcc tgagagggtt atgtttgtgc ttgctagctt      1260
tgctgttttgt tccatccagc acattcagtt ctgtttgaat cactttgctg caaatgtata      1320
tgtcgggcca ccgagtggga atgactggtt tgagaagcag acaagtggta cattggatat      1380
ctcttgtgcc tcttcgatgg attggttttt cggtggcttg cagtttcagc ttgagcatca      1440
tttgtttcca aggctaccct ggtgccaatt gaggaagatt tcgcctttgg ttagtgacct      1500
ttgcaagaag cataatttgc cttataggag cttgtcattt tgggaggcca atcagtggac      1560
aattaggacc ctcaggactg ctgccctaca agctagggac ttaacaaacc ctgcccctaa      1620
gaatttgttg tgggaagctg ttaatacccca tggctgaggc atttggagtt tttagagttt      1680
aggattttgt caaggtcttt tttttttttg ttttctcttt aaaaagaaaa aaaattctca      1740
ttgtgatttt gctagccccc acttttccag attgggcttt gaatttaact ttttgttagg      1800
tgtggtgtac aaatggatgg tgatccagat gttactgcag ttcatgtgct ttgcatcaat      1860
acaaattcat atcatgtatg ccaaaaaaaa aaaaaaaaaa aaaaaaaaaa aaaaaaaaaa      1920
aaaaaaaaaa aaaa                                                        1934
```

<210> SEQ ID NO 8
<211> LENGTH: 450
<212> TYPE: PRT
<213> ORGANISM: Glycine max

<400> SEQUENCE: 8

```
Met Glu Val Val Glu Lys Glu Lys Tyr Ile Thr Ser Glu Glu Leu
  1               5                  10                  15

Lys Gly His Asn Lys Glu Gly Asp Leu Trp Ile Ser Ile Gln Gly Lys
                 20                  25                  30

Val Tyr Asn Val Ser Asp Trp Val Lys Glu His Pro Gly Gly Asp Val
             35                  40                  45

Pro Ile Ser Asn Leu Ala Gly Gln Asp Val Thr Asp Ala Phe Ile Ala
         50                  55                  60

Tyr His Pro Gly Thr Ala Trp Ser His Leu Glu Lys Phe Phe Thr Gly
```

```
                65                  70                  75                  80
Tyr His Leu Ser Asp Phe Lys Val Ser Glu Val Ser Lys Asp Tyr Arg
                        85                  90                  95
Lys Leu Ala Ser Glu Phe Ser Lys Leu Gly Leu Phe Asp Thr Lys Gly
                100                 105                 110
His Val Thr Ser Cys Thr Leu Ala Ser Val Ala Val Met Phe Leu Ile
                115                 120                 125
Val Leu Tyr Gly Val Leu Arg Cys Thr Ser Val Trp Ala His Leu Gly
            130                 135                 140
Ser Gly Met Leu Leu Gly Leu Leu Trp Met Gln Ser Ala Tyr Val Gly
145                 150                 155                 160
His Asp Ser Gly His Tyr Val Val Met Thr Thr Asn Gly Phe Asn Lys
                165                 170                 175
Val Ala Gln Ile Leu Ser Gly Asn Cys Leu Thr Gly Ile Ser Ile Ala
                180                 185                 190
Trp Trp Lys Trp Thr His Asn Ala His His Ile Ala Cys Asn Ser Leu
            195                 200                 205
Asp His Asp Pro Asp Leu Gln His Met Pro Val Phe Ala Val Ser Ser
210                 215                 220
Arg Phe Phe Asn Ser Ile Thr Ser His Phe Tyr Gly Arg Lys Leu Glu
225                 230                 235                 240
Phe Asp Phe Ile Ala Arg Phe Leu Ile Cys Tyr Gln His Phe Thr Phe
                245                 250                 255
Tyr Pro Val Met Cys Val Ala Arg Val Asn Leu Tyr Leu Gln Thr Ile
                260                 265                 270
Leu Leu Leu Phe Ser Arg Arg Lys Val Gln Asp Arg Ala Leu Asn Ile
            275                 280                 285
Met Gly Ile Leu Val Phe Trp Thr Trp Phe Pro Leu Leu Val Ser Cys
            290                 295                 300
Leu Pro Asn Trp Pro Glu Arg Val Met Phe Val Leu Ala Ser Phe Ala
305                 310                 315                 320
Val Cys Ser Ile Gln His Ile Gln Phe Cys Leu Asn His Phe Ala Ala
                325                 330                 335
Asn Val Tyr Val Gly Pro Pro Ser Gly Asn Asp Trp Phe Glu Lys Gln
                340                 345                 350
Thr Ser Gly Thr Leu Asp Ile Ser Cys Ala Ser Ser Met Asp Trp Phe
            355                 360                 365
Phe Gly Gly Leu Gln Phe Gln Leu Glu His His Leu Phe Pro Arg Leu
            370                 375                 380
Pro Arg Cys Gln Leu Arg Lys Ile Ser Pro Leu Val Ser Asp Leu Cys
385                 390                 395                 400
Lys Lys His Asn Leu Pro Tyr Arg Ser Leu Ser Phe Trp Glu Ala Asn
                405                 410                 415
Gln Trp Thr Ile Arg Thr Leu Arg Thr Ala Ala Leu Gln Ala Arg Asp
            420                 425                 430
Leu Thr Asn Pro Ala Pro Lys Asn Leu Leu Trp Glu Ala Val Asn Thr
            435                 440                 445
His Gly
    450

<210> SEQ ID NO 9
<211> LENGTH: 1972
<212> TYPE: DNA
<213> ORGANISM: Triticum aestivum
```

-continued

```
<400> SEQUENCE: 9
gcacgagctc cctaacaaac ctccgttgct gttttaagat ccgatctccc cttccccct      60
cccctccctt cctcctgagt cctgaccacc cctcctcgcg ctccagctaa atccacgcca    120
ccgatggccc gcacgggcct cgcggacgca acggcgccgg aagccgacgc aatgccggcc    180
gccagcaagg acgccgccga cgtccgcatg atctccacca aggagctgca ggcgcacgct    240
gccgcggacg acctctggat ctccatctcc ggggacgtct acgacgtcac gccgtggctg    300
cgccaccacc cggcggcga gtcccgctc atcaccctcg ccggccagga cgccaccgac    360
gccttcatgg cctaccaccc gccctccgtg cgcccgctcc tccgccgctt cttcgtcggc    420
cgcctctccg actacaccgt ccccccgcc tccgccgact ccgccgcct cctcgcgcag    480
ctctcctccg cgggcctctt cgagcgcgtc ggccacaccc caagttcct gctcgtcgca    540
atgtcggtgc tcttctgcat cgccctctac tgcgtcctcg cctgctccag caccggggcc    600
cacatgttcg ccggcggcct cattggcttc atctggatcc agtcgggctg gattggccat    660
gactccggcc accaccaaat caccaggcac cccgcgctca accgcctcct gcaggtggtc    720
tccgggaact gcctcaccgg cctcggcatc gcctggtgga agttcaacca caacacacac    780
cacatctcct gcaacagcct cgaccatgac ccggacctcc agcacttgcc gctcttcgcg    840
gtttccacca agctcttcaa caacctttgg tcggtctgct acgagcgcac cttggcgttt    900
gatgccatat ccaagttctt cgtcagctac cagcactgga cattctaccc ggtgatggga    960
tttgcaagga taaatcttct tgtgcagtca atcgtgttcc tgatcacgca aagaaggtg    1020
cggcagcgtt ggctggagat cgccggagtt gcagcgttct gggtttggta ccccttgctg    1080
gtctcttgcc tgccgaattg gtgggagagg gttgcttttg tgcttgcaag ctttgtgatc    1140
acggggattc agcatgttca gttctgcctg aaccactct catccgctgt gtatgttggg    1200
ccaccaaagg ggaacgactg gtttgagagg caaacagcgg gcacacttga tatcaagtgc    1260
tccccgtgga tggattggtt ccatggtggt ctgcagttcc aggttgaaca ccatttgttt    1320
cctcgcctgc ctcgctgcca ctataggatg tcgcgccga ttgtgcgtga cctttgcaag    1380
aagcatgggc tgtcttatgg tgccgccaca ttctgggagg caaatgtaat gacatggaag    1440
acgctaaggc ctgcagcatt gcaggccagg aagccacta ctggagctgc tccaaagaat    1500
ctggtctggg aagctttgaa cactcatgga tgactgggat caggactgga gtatgagaca    1560
attgtaagcg tcgagccttg cgtgcatgca gttatctgat tgcttctcga ttgcgtagag    1620
atattgatcc ttttagctgt tggaatcgtg ttggattttt cgtgttgcca ggtgactatc    1680
tttgcagttc aatcgtgggt tcatgcttca gttgtgtact tgtacaccat atttagattg    1740
ttgggttctc cctatcatgg taactacatc aatagtactt gatttacatc ataaaatccg    1800
tggcttatct ttacatccat ttcattttgc ttgcaagttc atgaaactgt aaactcaatt    1860
gatggtttgt agcgtgtata tcctgctgct atggcagctt gaactgcatt ttgggaacat    1920
gacgattcca ataataaacg tttagacatt ttctaaaaaa aaaaaaaaaa aa            1972
```

<210> SEQ ID NO 10
<211> LENGTH: 469
<212> TYPE: PRT
<213> ORGANISM: Triticum aestivum

<400> SEQUENCE: 10

```
Met Ala Arg Thr Gly Leu Ala Asp Ala Thr Ala Pro Glu Ala Asp Ala
 1               5                  10                  15
```

-continued

Met Pro Ala Ala Ser Lys Asp Ala Ala Asp Val Arg Met Ile Ser Thr
                20                  25                  30

Lys Glu Leu Gln Ala His Ala Ala Ala Asp Asp Leu Trp Ile Ser Ile
            35                  40                  45

Ser Gly Asp Val Tyr Asp Val Thr Pro Trp Leu Arg His His Pro Gly
        50                  55                  60

Gly Glu Val Pro Leu Ile Thr Leu Ala Gly Gln Asp Ala Thr Asp Ala
65                  70                  75                  80

Phe Met Ala Tyr His Pro Pro Ser Val Arg Pro Leu Leu Arg Arg Phe
                85                  90                  95

Phe Val Gly Arg Leu Ser Asp Tyr Thr Val Pro Pro Ala Ser Ala Asp
            100                 105                 110

Phe Arg Arg Leu Leu Ala Gln Leu Ser Ser Ala Gly Leu Phe Glu Arg
        115                 120                 125

Val Gly His Thr Pro Lys Phe Leu Leu Val Ala Met Ser Val Leu Phe
    130                 135                 140

Cys Ile Ala Leu Tyr Cys Val Leu Ala Cys Ser Ser Thr Gly Ala His
145                 150                 155                 160

Met Phe Ala Gly Gly Leu Ile Gly Phe Ile Trp Ile Gln Ser Gly Trp
                165                 170                 175

Ile Gly His Asp Ser Gly His His Gln Ile Thr Arg His Pro Ala Leu
            180                 185                 190

Asn Arg Leu Leu Gln Val Val Ser Gly Asn Cys Leu Thr Gly Leu Gly
        195                 200                 205

Ile Ala Trp Trp Lys Phe Asn His Asn Thr His His Ile Ser Cys Asn
    210                 215                 220

Ser Leu Asp His Asp Pro Asp Leu Gln His Leu Pro Leu Phe Ala Val
225                 230                 235                 240

Ser Thr Lys Leu Phe Asn Asn Leu Trp Ser Val Cys Tyr Glu Arg Thr
                245                 250                 255

Leu Ala Phe Asp Ala Ile Ser Lys Phe Phe Val Ser Tyr Gln His Trp
            260                 265                 270

Thr Phe Tyr Pro Val Met Gly Phe Ala Arg Ile Asn Leu Leu Val Gln
        275                 280                 285

Ser Ile Val Phe Leu Ile Thr Gln Lys Lys Val Arg Gln Arg Trp Leu
    290                 295                 300

Glu Ile Ala Gly Val Ala Ala Phe Trp Val Trp Tyr Pro Leu Leu Val
305                 310                 315                 320

Ser Cys Leu Pro Asn Trp Trp Glu Arg Val Ala Phe Val Leu Ala Ser
                325                 330                 335

Phe Val Ile Thr Gly Ile Gln His Val Gln Phe Cys Leu Asn His Phe
            340                 345                 350

Ser Ser Ala Val Tyr Val Gly Pro Pro Lys Gly Asn Asp Trp Phe Glu
        355                 360                 365

Arg Gln Thr Ala Gly Thr Leu Asp Ile Lys Cys Ser Pro Trp Met Asp
    370                 375                 380

Trp Phe His Gly Gly Leu Gln Phe Gln Val Glu His His Leu Phe Pro
385                 390                 395                 400

Arg Leu Pro Arg Cys His Tyr Arg Met Val Ala Pro Ile Val Arg Asp
                405                 410                 415

Leu Cys Lys Lys His Gly Leu Ser Tyr Gly Ala Ala Thr Phe Trp Glu
            420                 425                 430

-continued

```
Ala Asn Val Met Thr Trp Lys Thr Leu Arg Ala Ala Leu Gln Ala
        435                 440                 445

Arg Glu Ala Thr Thr Gly Ala Ala Pro Lys Asn Leu Val Trp Glu Ala
450                 455                 460

Leu Asn Thr His Gly
465
```

<210> SEQ ID NO 11
<211> LENGTH: 448
<212> TYPE: PRT
<213> ORGANISM: Borago officinalis

<400> SEQUENCE: 11

```
Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
                20                  25                  30

Asp Val Ser Asp Trp Val Lys Asp His Pro Gly Gly Ser Phe Pro Leu
            35                  40                  45

Lys Ser Leu Ala Gly Gln Glu Val Thr Asp Ala Phe Val Ala Phe His
        50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
    210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala His Glu Leu Leu Gly
        275                 280                 285

Cys Leu Val Phe Ser Ile Trp Tyr Pro Leu Leu Val Ser Cys Leu Pro
    290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335
```

```
Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
            355                 360                 365

Gly Leu Gln Phe Gln Ile Glu His His Leu Phe Pro Lys Met Pro Arg
            370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
                420                 425                 430

Lys Pro Leu Pro Lys Asn Leu Val Trp Glu Ala Leu His Thr His Gly
            435                 440                 445

<210> SEQ ID NO 12
<211> LENGTH: 469
<212> TYPE: PRT
<213> ORGANISM: Triticum aestivum

<400> SEQUENCE: 12

Met Ala Arg Thr Gly Leu Ala Asp Ala Thr Ala Pro Glu Ala Asp Ala
1               5                   10                  15

Met Pro Ala Ala Ser Lys Asp Ala Ala Asp Val Arg Met Ile Ser Thr
            20                  25                  30

Lys Glu Leu Gln Ala His Ala Ala Asp Asp Leu Trp Ile Ser Ile
            35                  40                  45

Ser Gly Asp Val Tyr Asp Val Thr Pro Trp Leu Arg His His Pro Gly
        50                  55                  60

Gly Glu Val Pro Leu Ile Thr Leu Ala Gly Gln Asp Ala Thr Asp Ala
65                  70                  75                  80

Phe Met Ala Tyr His Pro Pro Ser Val Arg Pro Leu Leu Arg Arg Phe
                85                  90                  95

Phe Val Gly Arg Leu Thr Asp Tyr Thr Val Pro Pro Ala Ser Ala Asp
            100                 105                 110

Phe Arg Arg Leu Leu Ala Gln Leu Ser Ser Ala Gly Leu Phe Glu Arg
        115                 120                 125

Val Gly His Thr Pro Lys Phe Leu Leu Val Ala Met Ser Val Leu Phe
130                 135                 140

Cys Ile Ala Leu Tyr Cys Val Leu Ala Cys Ser Ser Thr Gly Ala His
145                 150                 155                 160

Met Phe Ala Gly Gly Leu Ile Gly Phe Ile Trp Ile Gln Ser Gly Trp
                165                 170                 175

Ile Gly His Asp Ser Gly His His Gln Ile Thr Arg His Pro Ala Leu
            180                 185                 190

Asn Arg Leu Leu Gln Val Val Ser Gly Asn Cys Leu Thr Gly Leu Gly
        195                 200                 205

Ile Ala Trp Trp Lys Phe Asn His Asn Thr His His Ile Ser Cys Asn
        210                 215                 220

Ser Leu Asp His Asp Pro Asp Leu Gln His Leu Pro Leu Phe Ala Val
225                 230                 235                 240

Ser Thr Lys Leu Phe Asn Asn Leu Trp Ser Val Cys Tyr Glu Arg Thr
                245                 250                 255

Leu Ala Phe Asp Ala Ile Ser Lys Phe Phe Val Ser Tyr Gln His Trp
```

```
                260                 265                 270
Thr Phe Tyr Pro Val Met Gly Phe Ala Arg Ile Asn Leu Leu Val Gln
            275                 280                 285
Ser Ile Val Phe Leu Ile Thr Gln Lys Lys Val Arg Gln Arg Trp Leu
        290                 295                 300
Glu Ile Ala Gly Val Ala Ala Phe Trp Val Trp Tyr Pro Leu Leu Val
305                 310                 315                 320
Ser Cys Leu Pro Asn Trp Trp Glu Arg Val Ala Phe Val Leu Ala Ser
                325                 330                 335
Phe Val Ile Thr Gly Ile Gln His Val Gln Phe Cys Leu Asn His Phe
            340                 345                 350
Ser Ser Ala Val Tyr Val Gly Pro Pro Lys Gly Asn Asp Trp Phe Glu
        355                 360                 365
Arg Gln Thr Ala Gly Thr Leu Asp Ile Lys Cys Ser Pro Trp Met Asp
370                 375                 380
Trp Phe His Gly Gly Leu Gln Phe Gln Val Glu His His Leu Phe Pro
385                 390                 395                 400
Arg Leu Pro Arg Cys His Tyr Arg Met Val Ala Pro Ile Val Arg Asp
                405                 410                 415
Leu Cys Lys Lys His Gly Leu Ser Tyr Gly Ala Ala Thr Phe Trp Glu
            420                 425                 430
Ala Asn Val Met Thr Trp Lys Thr Leu Arg Ala Ala Leu Gln Ala
        435                 440                 445
Arg Glu Ala Thr Thr Gly Ala Ala Pro Lys Asn Leu Val Trp Glu Ala
    450                 455                 460
Leu Asn Thr His Gly
465

<210> SEQ ID NO 13
<211> LENGTH: 458
<212> TYPE: PRT
<213> ORGANISM: Helianthus annuus

<400> SEQUENCE: 13

Met Val Ser Pro Ser Ile Glu Val Leu Asn Ser Ile Ala Asp Gly Lys
1               5                   10                  15
Lys Tyr Ile Thr Ser Lys Glu Leu Lys Lys His Asn Asn Pro Asn Asp
            20                  25                  30
Leu Trp Ile Ser Ile Leu Gly Lys Val Tyr Asn Val Thr Glu Trp Ala
        35                  40                  45
Lys Glu His Pro Gly Gly Asp Ala Pro Leu Ile Asn Leu Ala Gly Gln
    50                  55                  60
Asp Val Thr Asp Ala Phe Ile Ala Phe His Pro Gly Thr Ala Trp Lys
65                  70                  75                  80
His Leu Asp Lys Leu Phe Thr Gly Tyr His Leu Lys Asp Tyr Gln Val
                85                  90                  95
Ser Asp Ile Ser Arg Asp Tyr Arg Lys Leu Ala Ser Glu Phe Ala Lys
            100                 105                 110
Ala Gly Met Phe Glu Lys Lys Gly His Gly Val Ile Tyr Ser Leu Cys
        115                 120                 125
Phe Val Ser Leu Leu Ser Ala Cys Val Tyr Gly Val Leu Tyr Ser
    130                 135                 140
Gly Ser Phe Trp Ile His Met Leu Ser Gly Ala Ile Leu Gly Leu Ala
145                 150                 155                 160
```

```
Trp Met Gln Ile Ala Tyr Leu Gly His Asp Ala Gly His Tyr Gln Met
                165                 170                 175

Met Ala Thr Arg Gly Trp Asn Lys Phe Ala Gly Ile Phe Ile Gly Asn
            180                 185                 190

Cys Ile Thr Gly Ile Ser Ile Ala Trp Trp Lys Trp Thr His Asn Ala
        195                 200                 205

His His Ile Ala Cys Asn Ser Leu Asp Tyr Asp Pro Asp Leu Gln His
    210                 215                 220

Leu Pro Met Leu Ala Val Ser Ser Lys Leu Phe Asn Ser Ile Thr Ser
225                 230                 235                 240

Val Phe Tyr Gly Arg Gln Leu Thr Phe Asp Pro Leu Ala Arg Phe Phe
                245                 250                 255

Val Ser Tyr Gln His Tyr Leu Tyr Tyr Pro Ile Met Cys Val Ala Arg
            260                 265                 270

Val Asn Leu Tyr Leu Gln Thr Ile Leu Leu Leu Ile Ser Lys Arg Lys
        275                 280                 285

Ile Pro Asp Arg Gly Leu Asn Ile Leu Gly Thr Leu Ile Phe Trp Thr
    290                 295                 300

Trp Phe Pro Leu Leu Val Ser Arg Leu Pro Asn Trp Pro Glu Arg Val
305                 310                 315                 320

Ala Phe Val Leu Val Ser Phe Cys Val Thr Gly Ile Gln His Ile Gln
                325                 330                 335

Phe Thr Leu Asn His Phe Ser Gly Asp Val Tyr Val Gly Pro Pro Lys
            340                 345                 350

Gly Asp Asn Trp Phe Glu Lys Gln Thr Arg Gly Thr Ile Asp Ile Ala
        355                 360                 365

Cys Ser Ser Trp Met Asp Trp Phe Phe Gly Gly Leu Gln Phe Gln Leu
    370                 375                 380

Glu His His Leu Phe Pro Arg Leu Pro Arg Cys His Leu Arg Ser Ile
385                 390                 395                 400

Ser Pro Ile Cys Arg Glu Leu Cys Lys Lys Tyr Asn Leu Pro Tyr Val
                405                 410                 415

Ser Leu Ser Phe Tyr Asp Ala Asn Val Thr Thr Leu Lys Thr Leu Arg
            420                 425                 430

Thr Ala Ala Leu Gln Ala Arg Asp Leu Thr Asn Pro Ala Pro Gln Asn
        435                 440                 445

Leu Ala Trp Glu Ala Phe Asn Thr His Gly
    450                 455

<210> SEQ ID NO 14
<211> LENGTH: 35
<212> TYPE: DNA
<213> ORGANISM: Artificial Sequence
<220> FEATURE:
<223> OTHER INFORMATION: Definition of Artificial Sequence:PCR primer
      for 5' of pk0011.d5

<400> SEQUENCE: 14
tttgcggccg caaatcaatg gaagaagcaa  agaag                              35

<210> SEQ ID NO 15
<211> LENGTH: 33
<212> TYPE: DNA
<213> ORGANISM: Artificial Sequence
<220> FEATURE:
<223> OTHER INFORMATION: Definition of Sequence: antisense PCR primer
      for 3' of pk0011.d5
```

```
<400> SEQUENCE: 15
tttgcggccg ccaggattca cccgaaagtg ttc                                   33

<210> SEQ ID NO 16
<211> LENGTH: 823
<212> TYPE: DNA
<213> ORGANISM: Triticum aestivum
<220> FEATURE:
<221> NAME/KEY: unsure
<222> LOCATION: (48)
<223> OTHER INFORMATION: n = A, C, G, or T
<220> FEATURE:
<221> NAME/KEY: unsure
<222> LOCATION: (538)
<223> OTHER INFORMATION: n = A, C, G, or T
<220> FEATURE:
<221> NAME/KEY: unsure
<222> LOCATION: (686)
<223> OTHER INFORMATION: n = A, C, G, or T
<220> FEATURE:
<221> NAME/KEY: unsure
<222> LOCATION: (704)
<223> OTHER INFORMATION: n = A, C, G, or T
<220> FEATURE:
<221> NAME/KEY: unsure
<222> LOCATION: (717)
<223> OTHER INFORMATION: n = A, C, G, or T
<220> FEATURE:
<221> NAME/KEY: unsure
<222> LOCATION: (727)
<223> OTHER INFORMATION: n = A, C, G, or T
<220> FEATURE:
<221> NAME/KEY: unsure
<222> LOCATION: (729)
<223> OTHER INFORMATION: n = A, C, G, or T
<220> FEATURE:
<221> NAME/KEY: unsure
<222> LOCATION: (737)
<223> OTHER INFORMATION: n = A, C, G, or T
<220> FEATURE:
<221> NAME/KEY: unsure
<222> LOCATION: (741)
<223> OTHER INFORMATION: n = A, C, G, or T
<220> FEATURE:
<221> NAME/KEY: unsure
<222> LOCATION: (750)..(751)
<223> OTHER INFORMATION: n = A, C, G, or T
<220> FEATURE:
<221> NAME/KEY: unsure
<222> LOCATION: (769)
<223> OTHER INFORMATION: n = A, C, G, or T
<220> FEATURE:
<221> NAME/KEY: unsure
<222> LOCATION: (777)
<223> OTHER INFORMATION: n = A, C, G, or T
<220> FEATURE:
<221> NAME/KEY: unsure
<222> LOCATION: (807)
<223> OTHER INFORMATION: n = A, C, G, or T

<400> SEQUENCE: 16
ctccctaaca aacctccgtt gctgttttaa gatccgatct ccccttcncc cctccctcc       60 cttcctcctg agtcctgacc acccctcctc gcgctccagc taaatccacg ccaccgatgg    120
cccgcacggg cttcgcggac gcaacggcgc cggaagccga cgcaatgccg gccgccagca    180
aggacgccgc cgacgtccgc atgatctcca ccaaggagct gcaggcgcac gccgccgcgg    240
acgacctctg gatctccatc tccggggacg tctacgacgt cacgccctgg ctgcgccacc    300
acccgggcgg cgaggtcccg ctcatcaccc tcgccggcca ggacgccacc gacgccttca    360
tggcctacca cccgccctcc gtgcgccgc tcctccgcg cttcttcgtc ggccgcctca    420
ccgactacac tgtccccccc gcctccgccg acttcgccg cctcctcgcg cagctctcct    480
```

```
ccgcgggcct cttcgagcgc gtcggcacac ccccaagttc ctgctcgtcg caaagtcngt      540
gctcttctgc atcggcctct actgctcctc gcctgctcaa caccggggcc acatgttcgc      600
cgggggctca ttggcttatc tggtcagtcg ggctggattg gcatactccg gcacacaaat      660
cacaggcacc tgcctcaacg ctctgnagtg gctcgggaat gctnacggct cggatcnctg      720
gggagtnanc acacaanaca nattctgaan ngtcacatac ctgactcana ttccgtntcg      780
ggtcacaagt ctaaaacttg catcgtnaag acttggttag cat                        823
```

<210> SEQ ID NO 17
<211> LENGTH: 114
<212> TYPE: PRT
<213> ORGANISM: Triticum aestivum

<400> SEQUENCE: 17

```
Met Pro Ala Ala Ser Lys Asp Ala Ala Asp Val Arg Met Ile Ser Thr
 1               5                  10                  15

Lys Glu Leu Gln Ala His Ala Ala Asp Asp Leu Trp Ile Ser Ile
            20                  25                  30

Ser Gly Asp Val Tyr Asp Val Thr Pro Trp Leu Arg His His Pro Gly
        35                  40                  45

Gly Glu Val Pro Leu Ile Thr Leu Ala Gly Gln Asp Ala Thr Asp Ala
    50                  55                  60

Phe Met Ala Tyr His Pro Pro Ser Val Arg Pro Leu Leu Arg Arg Phe
65                  70                  75                  80

Phe Val Gly Arg Leu Thr Asp Tyr Thr Val Pro Pro Ala Ser Ala Asp
                85                  90                  95

Phe Arg Arg Leu Leu Ala Gln Leu Ser Ser Ala Gly Leu Phe Glu Arg
               100                 105                 110

Val Gly
```

US 6,864,077 B1

MEMBRANE-BOUND DESATURASES

This application is a 371 of PCT/US99/28589 filed Dec. 2, 1999 which claims the benefit of U.S. Provisional Application No. 60/110,784 filed Dec. 3, 1998.

FIELD OF THE INVENTION

This invention is in the field of plant molecular biology. More specifically, this invention pertains to nucleic acid fragments encoding delta-6 desaturase or sphingolipid desaturase in plants and seeds.

BACKGROUND OF THE INVENTION

Polyunsaturated fatty acids are of major importance in animal health as they have roles in the maintenance of membrane structure and function, in the regulation of cholesterol synthesis and transport, in the prevention of water loss from the skin, and as precursors of eicosanoids, including prostaglandins and leucotrienes. In animals, members of this class of fatty acids are synthesized from the essential fatty acid linoleic acid (C18:2$\Delta^{9,12}$), the first step being the desaturation to gamma-linolenic acid (GLA; C18:3$\Delta^{6,9,12}$) catalyzed by delta-6 desaturase. Clinical trials have shown that dietary supplementation of GLA may be effective in treating a number of ailments (e.g., atopic eczema, mastalgia, diabetic neuropathy, viral infections, and some types of cancer) (Jiang et al. (1998) *Crit. Rev. Oncol. Hematol.* 27:179–209; Kruger, and Horrobin (1997) *Prog. Lipid Res.* 36:131–51). Oils containing GLA are therefore widely used as a general health supplement and have been registered for pharmaceutical use.

In the plant kingdom, GLA is an uncommon fatty acid. Major commercial sources of GLA are evening primroses (*Oenothera* spp.), in which GLA accounts for about 8 to 10% of the seed oil, and borage (starflower: *Borago officinalis*) wherein seeds contain some 20 to 25% GLA. These plants, however, suffer from poor agronomic performance and low yield. There is therefore considerable interest in increasing the GLA content of existing crops and in producing GLA in a conventional oil crop. Expression of a cDNA encoding the delta-6 fatty acid desaturase from developing seeds of borage in transgenic tobacco plants resulted in accumulation of GLA and octadecatetraenoic acid (C18:4 $\Delta^{6,9,12,15}$) to levels of 13.2% and 9.6% of the total fatty acids, respectively. The borage delta-6 fatty acid desaturase differs from other previously characterized higher plant desaturase enzymes by the presence of an N-terminal domain related to cytochrome b5 (Sayanova et al. (1997) *Proc. Natl. Acad Sci USA* 94:4211–4216). This desaturase does not appear to have an N-terminal cleavable endoplasmic reticulum-targeting signal, but the hydrophobic regions present in the protein would be sufficient to allow it to associate with the endomembrane system. A tripartite motif containing eight conserved histidines has been identified in almost all membrane desatuases (HX$_{(3-4)}$HX$_{(7-4)}$HX$_{(2-3)}$HHX$_{(61-189)}$HX$_{(2-3)}$HH). In *Anabaena* and borage delta-6 desaturase a glutamine residue replaces the first histidine of the third element.

Membrane and reserve lipids of plants contain fatty acids with different degrees of unsaturation which are controlled by different desaturase enzymes. A cDNA isolated from ripening sunflower embryos encodes a protein with the conserved three histidine domains characteristic of membrane-bound desaturases. This cDNA also encodes a fusion protein composed of an N-terminal cytochrome b5 and a domain similar to membrane-bound acyl lipid desaturases (Sperling et al. (1995) *Eur. J. Biochem.* 232:798–805). Expression of homologous cDNAs from *Brassica napus* and *Arabidopsis thaliana* in *Saccharomyces cerevisiae* results in significant proportions of new $\Delta^{8,9}$-cis/trans-phytosphingenines that accompany the residual C$_{18}$-phytosphinganine predominating in wild-type yeast cells. These genes encode new members of the cytochrome b5 superfamily which function as a stereounselective sphingolipid desaturase and show trans-activity (Sperling et al. (1998) *J. Biol. Chem.* 273: 28590–28596).

The enzymes encoded by the *picramnia* cDNAs included in this application possibly catalyze the formation of a triple bond since *picramnia* seeds accumulate large amounts of tariric acid (18:1 delta-6-acetylenic), an unusual fatty acid that has a triple bond (or acetylenic bond) at the delta-6 carbon. Tariric acid has many of the same industrial uses ascribed to petroselenic acid, thus these cDNAs should be useful in the production of novel fatty acids in the seed oils of transgenic plants. Although with similarities to the delta-6 desaturase, the enzymes encoded by the corn, soybean, and wheat sequences described herein are sphingolipid desaturases since these plants do not produce delta 6 double bonds like *picramnia* and borage.

SUMMARY OF THE INVENTION

The present invention relates to isolated polynucleotides comprising a nucleotide sequence encoding a first polypeptide of at least 60 amino acids that has at least 55% identity based on the Clustal method of alignment when compared to a Florida bitterbush delta-6 desaturase polypeptide of SEQ. ID NO:2, and an isolated polynucleotide comprising a nucleotide sequence encoding a first polypeptide of at least 114 amino acids that has at least 80% identity based on the Clustal method of alignment when compared to a polypeptide selected from the group consisting of a corn sphingolipid desaturase polypeptide of SEQ ID NO:4, a soybean sphingolipid desaturase polypeptide of SEQ ID NOs:6 and 8, a wheat sphingolipid desaturase polypeptide of SEQ ID NO:10 and SEQ ID NO:17. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, and 16, that codes for the polypeptide selected from the group consisting of SEQ ID NOs:2, 4, 6, 8, and 17. The present invention also relates to an isolated polynucleotide comprising a nucleotide sequences of at least 60 (preferably at least 40, most preferably at least 30) contiguous nucleotides derived from a nucleotide sequence selected from the group consisting of SEQ ID NOs:1, 3, 5, 7, and 16, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a delta-6 desaturase polypeptide of at least 60 amino acids comprising at least 55% homology based on the Clustal method of alignment compared to the polypeptide of SEQ ID NO:2, or a sphingolipid desaturase polypeptide of at least 114 amino acids comprising at least 80% homology based on the Clustal method of alignment compared to a polypeptide selected from the group consisting of SEQ ID NOs:4, 6, 8, and 17.

The present invention relates to a method of selecting an isolated polynucleotide that affects the level of expression of a delta-6 desaturase or sphingolipid desaturase polypeptide in a host cell, preferably a plant cell, the method comprising the steps of
(a) constructing an isolated polynucleotide of the present invention or an isolated chimeric gene of the present invention;
(b) introducing the isolated polynucleotide or the isolated chimeric gene into a host cell;
(c) measuring the level a delta-6 desaturase or sphingolipid desaturase polypeptide in the plant cell containing the isolated polynucleotide; and
(d) comparing the level of a deltas desaturase or sphingolipid desaturase polypeptide in the host cell containing the isolated polynucleotide with the level of a delta-6 desaturase or sphingolipid desaturase polypeptide in a host cell that does not contain the isolated polynucleotide.

The present invention relates to a method of obtaining a nucleic acid fragment encoding a substantial portion of a delta-6 desaturase or sphingolipid desaturase polypeptide gene, preferably a plant delta-6 desaturase or sphingolipid desaturase polypeptide gene, comprising the steps of: synthesizing an oligonucleotide primer comprising a nucleotide sequence of at least 40 (preferably at least 30) contiguous nucleotides derived from a nucleotide sequence selected from the group consisting of SEQ ID NOs:1, 3, 5, 7, and 16, and the complement of such nucleotide sequences; and amplifying a nucleic acid fragment (preferably a cDNA inserted in a cloning vector) using the oligonucleotide primer. The amplified nucleic acid fragment preferably will encode a portion of a delta-6 desaturase or sphingolipid desaturase amino acid sequence.

The present invention also relates to a method of obtaining a nucleic acid fragment encoding all or a substantial portion of the amino acid sequence encoding a delta-6 desaturase or sphingolipid desaturase polypeptide comprising the steps of: probing a cDNA or genomic library with an isolated polynucleotide of the present invention; identifying a DNA clone that hybridizes with an isolated polynucleolide of the present invention; isolating the identified DNA clone; and sequencing the cDNA or genomic fragment that comprises the isolated DNA clone.

The present invention also relates to a method for positive selection of a transformed cell comprising:
(a) transforming a host cell with the chimeric gene of the present invention; and
(b) growing the transformed host cell under conditions suitable for the expression of the chimeric gene allowing expression of the polynucleotide in an amount to alter the concentration of fatty acids with delta-6 double bonds in the host cell to provide a positive selection means.

The present invention also relates to the method of the present invention wherein the host cell is selected from the group consisting of plant cells and procaryotes.

The present invention also relates to the method of the present invention wherein levels of tariric acid are altered.

The present invention also relates to a method for positive selection of a transformed cell comprising:
(a) transforming a plant cell with the chimeric gene of the present invention; and
(b) growing a plant from the transformed plant cell of step (a) allowing expression of the polynucleotide in an amount to alter the concentration of fatty acids with delta-6 double bonds in the seeds of the plant to provide a positive selection means.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A–C show a comparison of the amino acid sequences of the Florida bitterbush delta-6 desaturase from clone pps.pk0011.d5:fis (SEQ ID NO:2, denoted [SIN 2]), the soybean sphingolipid desaturase from clone ssl.pk0017.b4:fis (SEQ ID NO:8, denoted [SIN 8], the borage delta-6 desaturase having NCBI General Identification No. 2062403 (SEQ ID NO:11), corn sphingolipid desaturase from clone cde1c.pk001.o8:fis (SEQ ID NO:4, denoted [SIN 4]), wheat sphingolipid desaturase from clone wre1.pk0004.c7:fis (SEQ ID NO:10, denoted [SIN 10],) wheat delta-6 desaturase-like protein having NCBI General Identifier No. 4104056 (SEQ ID NO:12), soybean sphingolipid desaturase from the contig assembled of clones sfl1.pk0012.c5 and sfl1.pk0031.d11 (SEQ ID NO:6, denoted [SIN 6]), and sunflower having NCBI General Identifier No. 1040729 (SEQ ID NO:13).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Delta-6 Desaturase or Sphingolipid Desaturase

| | | SEQ ID NO: | |
|---|---|---|---|
| | Clone Designation | (Nucleotide) | (Amino Acid) |
| Delta-6 Fatty Acid Desaturase | | | |
| Bitterbush-Fl. [*Picramnia pentandra*] | pps.pk0011.d5:fis | 1 | 2 |
| Sphingolipid Desaturase | | | |
| Corn [*Zea mays*] | cde1c.pk001.o8:fis | 3 | 4 |
| Soybean [*Glycine max*] | Contig of: sfl1.pk0012.c5 sfl1.pk0031.d11 | 5 | 6 |
| Soybean [*Glycine max*] | ss1.pk0017.b4:fis | 7 | 8 |

TABLE 1-continued

Delta-6 Desaturase or Sphingolipid Desaturase

| | | SEQ ID NO: | |
|---|---|---|---|
| | Clone Designation | (Nucleo-tide) | (Amino Acid) |
| Wheat [*Triticum aestivum*] | wre1.pk0004.c7:fis | 9 | 10 |
| Wheat [*Triticum aestivum*] | wre1.pk0004.c7 | 16 | 17 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2); 345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least 40 contiguous nucleotides, most preferably at least 30 contiguous nucleotides, of the nucleic acid sequence of the SEQ ID NOs:1, 3, 5, 7, 9, 16, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least 30 contiguous nucleotides derived from a nucleotide sequence selected from the group consisting of SEQ ID NOs:1, 3, 5, 7, and 16, and the complement of such nucleotide sequences may be used in methods of selecting an isolated polynucleotide that affects the expression of a polypeptide such as a delta-6 fatty acid desaturase and/or a sphingolipid desaturase in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid*

Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min. and then repeated twice with 0.2×SSC. 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, VI). Multiple alignment of the sequences was performed using the Clustal method of alignment (Higgins and Sharp (1989) $CABIOS.$ 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) $J. Mol. Biol.$ 215:403–410 In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer.

Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (I 989) *Plant Cell* 1:671–680.

"RNA transcript" refers to the product resulting from RNA polymerase-catalyzed transcription of a DNA sequence. When the RNA transcript is a perfect complementary cop) of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed; organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e. one from which any pre- or propeptides present in the primary translation product have been removed. "Precursor" protein refers to the primary product of translation of mRNA; i.e. with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:7073; U.S. Pat. No. 4,945,050, incorporated herein by reference).

Standard recombinant DNA and molecular cloning techniques used herein are well known in the art and are described more fully in Sambrook et al. *Molecular Cloning. A Laboratory Manual*; Cold Spring Harbor Laboratory Press: Cold Spring Harbor, 1989 (hereinafter "Maniatis").

Nucleic acid fragments encoding at least a portion of several delta-6 desaturase or sphingolipid desaturase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other delta-6 desaturase or sphingolipid desaturases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably one of at least 30) contiguous nucleotides derived from a nucleotide sequence selected from the group consisting of SEQ ID NOs:1, 3, 5, 7, and 16 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as delta-6 desaturase or sphingolipid desaturase) preferably a substantial portion of a plant polypeptide of a gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, and 16, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the composition of fatty acids in those cells. Overexpression of delta-6 desaturase may allow the production of higher levels of tariric acid in *Picramnia*. Co-suppression of sphingolipid desaturase may allow for the production of higher levels of unsaturated corn and soybean oils.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by. Southern analysis of DNA. Northern analysis of mRNA expression. Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded delta-6 desaturase or sphingolipid desaturase. An example of a vector for high level expression of the instant polypeptides in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botsiein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:3741. Numerous publications describe genetic mapping of specific cDNA clones using the methodology outlined above or variations thereof. For example. F2 intercross populations, backcross populations, randomly mated populations, near isogenic lines, and other sets of individuals may be used for mapping. Such methodologies are well known to those skilled in the ar.

Nucleic acid probes derived from the instant nucleic acid sequences may also be used for physical mapping (i.e. placement of sequences on physical maps; see Hoheisel et al. In: *Nonmammalian Genomic Analysis: A Practical Guide.* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7: 149–154). Although current methods of FISH mapping favor use of large clones (several to several hundred KB; see Laan et al. (1995) *Genome Res.* 5: 13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al., (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402–9406; Koes et al. (1995) *Proc. Natl. Acad Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various Florida bitterbush, corn, soybean, and wheat tissues were prepared. The characteristics of the libraries are described below.

TABLE 2 cDNA Libraries from Florida Bitterbush, Corn, Soybean, and Wheat

| Library | Tissue | Clone |
|---------|--------|-------|
| pps | Developing Seeds of *Picramnia pentandra* (Florida bitterbush) | pps.pk0011.d5:fis |
| cde1c | Corn (*Zea mays*, B13) Developing Embryo 20 DAP | cde1c.pk001.08:fis |
| sfl1 | Soybean Immature Flower | sfl1.pk0031.d11 |
| ss1 | Soybean Seedling 5–10 Days After Germination | ss1.pk0017.b4:fis |
| wre1 | Wheat Root From 7 Day Old Etiolated Seedling | wre1.pk0004.c7:fis | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBlucscript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs": see Adams et al., (1991) *Science* 252:1651–1656). The resulting ESTs are analyzed using a Perkin Elmer Model 377 fluorescent sequencer.

Example 2

Identification of cDNA Clones cDNA clones encoding delta-6 desaturase or sphingolipid desaturase were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Delta-6 Desaturase

The BLASTX search using the EST sequences from clones listed in Table 3 revealed similarity of the polypeptides encoded by the cDNAs to delta-6 desaturase from borage [*Borago officinalis*] (NCBI General Identifier No. 2062403). Shown in Table 3 are the BLAST results for the sequences of the entire cDNA inserts comprising the indicated cDNA clones ("FIS"):

TABLE 3

BLAST Results for Sequences Encoding Polypeptides Homologous to Delta-6 Desaturase

| Clone | Status | BLAST pLog Score 2062403 |
|---|---|---|
| pps.pk0011.d5:fis | FIS | 132.00 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a delta-6 desaturase. These sequences represent the first *Picramnia pentandra* sequences encoding delta-6 desaturase.

Example 4

Characterization of cDNA Clones Encoding Sphingolipid Desaturase

The BLASTX search using the EST sequences from clones listed in Table 4 revealed similarity of the polypeptides encoded by the cDNAs to sphingolipid desaturase from borage [*Borago officinalis*] (NCBI General Identifier No. 2062403), wheat [*Triticum aestivum*] (NCBI General Identifier No. 4104056), and sunflower [*Helianthus annuus*] (NCBI General Identifier No. 1040729). Shown in Table 4 are the BLAST results for the sequences of the entire cDNA inserts comprising the indicated cDNA clones ("FIS"), or contigs assembled from two or more ESTs ("Contig"):

TABLE 4

BLAST Results for Sequences Encoding Polypeptides Homologous to Sphingolipid Desaturase

| Clone | Status | NCBI General Identifier No. | BLAST pLog Score |
|---|---|---|---|
| ss1.pk0017.b4:fis | FIS | 2062403 | 254.00 |
| cde1c.pk001.o8:fis | FIS | 4104056 | 254.00 |
| wre1.pk0004.c7:fis | FIS | 4104056 | 254.00 |
| sf11.pk0012.c5 sf11.pk0031.d11 | Contig | 1040729 | 88.00 |

FIGS. 1A–1C present an alignment of the amino acid sequences set forth in SEQ ID NOs:2, 4, 6, 8, and 10 and the borage sequence (SEQ ID NO:11), wheat sequence (SEQ ID NO:12), and sunflower sequence (SEQ ID NO:13). The data in Table 5 represents a calculation of the percent identity of the amino acid sequences set forth in SEQ ID NOs:2, 4, 6, 8, and 10, and the borage sequence (NCBI General Identifier No. 2062403, SEQ ID NO:11), wheat sequence (NCBI General Identifier No. 4104056, SEQ ID NO:12), and sunflower sequence (NCBI General Identifier No. 1040729, SEQ ID NO:13). The data in Table 5 represents a calculation of the percent identity of the amino acid sequence set forth in SEQ ID NOs:2, 4, 6, 8 and 10 and the delta 6 desaturase borage sequence (SEQ ID NO:11) and the wheat and sunflower sphingolipid desaturases (SEQ ID NOs:12 and 13, respectively.

TABLE 5

Percent Identity of Amino Acid Sequences Deduced From the Nucleotide Sequences of cDNA Clones Encoding Polypeptides Homologous to Delta-6 Desaturase and Sphingolipid Desaturase

| SEQ ID NO. | Percent Identity to | | |
|---|---|---|---|
| | 2062403 | 4104056 | 1040729 |
| 2 | 54.0 | 49.2 | 51.4 |
| 8 | 62.7 | 55.2 | 70.3 |
| 4 | 54.0 | 79.5 | 53.7 |
| 10 | 54.0 | 99.8 | 53.5 |
| 6 | 49.8 | 48.6 | 53.0 |

The wheat sequence that is a virtual match to SEQ ID NO:10 was deposited into NCBI on Jan. 29, 1999, almost two months after the priority date of the provisional filing of the present application. Therefore the wheat sequence that is claimed herein is the EST filed in the provisional application (herein labeled SEQ ID NO:17) that is comprised of amino acids 17–130 in SEQ ID NO:10.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a sphingolipid desaturase. These sequences represent the first monocot and first soybean sequences encoding sphingolipid desaturase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML 103 has been deposited under the terms of the Budapest Treaty at ATCC (American Type Culture Collection. 10801 University Blvd. Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL 1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH 132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the clamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the 0 subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker. 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose get by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly. MA). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 250. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Expression of *Picramnia* EST pps.pk0011.d5 in Somatic Soybean Embryos

As one method of assaying the function of the polypeptide encoded by the *Picramnia* EST pps.pk0011.d5, the corresponding cDNA was expressed in somatic soybean embryos, and the fatty acid composition of the resulting transgenic tissue was examined for alterations accompanying the expression of the cDNA.

A plasmid pZBL100 containing chimeric genes to allow expression of hygromycin B phosphotransferase in certain bacteria and in plant cells was constructed from the following genetic elements: (a) T7 promoter+Shine-Delgarno/hygromycin B phosphotransferase (HPT)/T7 terminator sequence, (b) 35S promoter from cauliflower mosaic virus (CaMV)/hygromycin B phosphotransferase (HPT)/nopaline synthase (NOS3' from Agrobacterium tumefaciens T-DNA, and (c) pSP72 plasmid vector [from Promega] with P-lactamase coding region (ampicillin resistance gene) removed.

The hygromycin B phosphotransferase gene was amplified by PCR from E. coli strain W677, which contained a Klebsiella derived plasmid pJR225. Starting with the pSP72 vector the elements were assembled into a single plasmid using standard cloning methods (Maniatis).

Plasmid pZBL100 thus contains the T7 promoter/HPT/T7 terminator cassette for expression of the HPT enzyme in certain strains of E. coli, such as NovaBlue (DE3) (Novagen), that are lysogenic for lambda DE3 (which carries the T7 RNA Polymerase gene under lacUV5 control). Plasmid pZBL100 also contains the $^{35}$S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems.

PZBL100 also contains three unique restriction endonuclease sites suitable for the cloning of other chimeric genes into this vector.

A plasmid for expression of the cDNA encoding fatty acid modifying enzymes under the control of the soybean β-conglycinin promoter (Beachy et al., (1985) EMBO J. 4:3047–3053) can be constructed. The construction of this vector was facilitated by the use of plasmids pCW109 and pML18, both of which have been described (see World Patent Publication No. WO 94/11516).

A unique NotI site was introduced into the cloning region between the β-conglycinin promoter and the phaseolin 3' end in pCW109 by digestion with NcoI and XbaI followed by removal of the single stranded DNA ends with mung bean exonuclease. NotI linkers (New England Biochemical catalog number NEB 1125) were ligated into the linearized plasmid to produce plasmid pAW35. The single NotI site in pML18 was destroyed by digestion with NotI, filling in the single stranded ends with dNTPs and Klenow fragment followed by re-ligation of the linearized plasmid. The modified pML18 was then digested with HindIII and treated with calf intestinal phosphatase.

The β-conglycinin:NotI:phaseolin expression cassette in pAW35 was removed by digestion with Hind III and the 1.8 kB fragment was isolated by agarose gel electrophoresis. The isolated fragment was ligated into the modified and linearized pML18 construction described above. A clone with the desired orientation was identified by digestion with NotI and XbaI to release a 1.08 kB fragment indicating that the orientation of the O-conglycinin transcription unit was the same as the selectable marker transcription unit. The resulting plasmid was given the name pBS19.

HindIII is one of the unique cloning sites available in pZBL100. To assemble the final expression cassette, pBS19 and pZBL100 were both digested with HindIII. The β-conglycinin containing fragment from pBS19 was isolated by gel electrophoresis and ligated into the digested pZBL100, which had been treated with calf alkaline phosphatase. The resulting plasmid was named pKS67.

The cDNA insert for the Picramnia EST pk0011.d5 was amplified by PCR to generate flanking NotI sites to allow for cloning into the corresponding restriction site of plasmid pKS67. The 5' and 3' oligonucleotide primers used for the amplification of the Picramnia cDNA are provided in SEQ ID NO:14 and 15, respectively.

PCR reactions were conducted using Pfu polymerase (Stratagene) and the cDNA corresponding to EST pps.pk0011.d5 as the template. Products from amplification reactions were purified and subcloned into pCR-Script Amp SK(+). The PCR product was then moved as a NotI fragment into the soybean expression vector pKS67.

Gene fusions of the Picramnia cDNA with the conglycinin promoter and phaseolin termination sequences in vector pKS67 were introduced into soybean embryos using the particle bombardment method of transformation. To induce somatic embryos, cotyledons, 3–5 mm in length dissected from surface sterilized, immature seeds of a soybean cultivar, such as A2872, can be cultured in the light or dark at 26° C. on an appropriate agar medium for 6–10 weeks. Somatic embryos that produce secondary embryos were then excised and placed into a suitable liquid medium. After repeated selection for clusters of somatic embryos that multiplied as early, globular staged embryos, the suspensions were maintained as described below.

Soybean embryogenic suspension cultures were maintained in 35 mL liquid media on a rotary shaker, 150 rpm, at 26° C. with fluorescent lights on a 16:8 hour day/night schedule. Cultures were subcultured every two weeks by inoculating approximately 35 mg of tissue into 35 mL of liquid medium.

Soybean embryogenic suspension cultures were then transformed with the vector pKS67 containing the Picramnia cDNA for EST pps.pk0011.d5 by the method of particle gun bombardment (Klein et al. (1987) Nature (London) 327:70, U.S. Pat. No. 4,945,050). A DuPont Biolistica PDS1000/HE instrument (helium retrofit) was used for these transformations.

To 50 mL of a 60 mg/mL 1 mm gold particle suspension were added (in order): 5 mL DNA (1 mg/mL), 20 ml spermidine (0.1 M), and 50 mL $CaCd_2$ (2.5 M). The particle preparation was then agitated for three minutes, spun in a microfuge for 10 seconds and the supernatant removed. The DNA-coated particles were then washed once in 400 mL 70% ethanol and resuspended in 40 mL of anhydrous ethanol. The DNA/particle suspension was sonicated three times for one second each. Five mL of the DNA-coated gold particles was then loaded on each macro carrier disk.

Approximately 300–400 mg of a two-week-old suspension culture was placed in an empty 60×1 5-mm petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded three times. Following bombardment, the tissue was divided in half and placed back into liquid and cultured as described above.

Five to seven days post bombardment, the liquid media was exchanged with fresh media, and eleven to twelve days post bombardment with fresh media containing 50 mg/mL hygromycin. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos.

Transgenic soybean embryos selected and maintained in this manner were analyzed for alterations in fatty acid composition. Individual embryos expressing the cDNA for the *Picramnia* EST pps.pk0011.d5 were homogenized in 1% (w/v) sodium methoxide in methanol. Fatty acid methyl esters resulting from this transesterification step were analyzed by both GC and GC-MS as described elsewhere (Hitz et al. (1994) Plant Physiol. 105:635–641). Using this methodology, individual somatic soybean embryos from transformation event MS151-5-4 were found to contain a fatty acid whose methyl ester had a retention time and mass spectrum consistent with that of gamma-linolenic acid ($18:3\Delta^{6,9,12}$). This fatty acid is not normally present in somatic soybean embryos. In individual embryos expressing the cDNA for *Picramnia* EST pps.pk0011.d5, gamma-linolenic acid was detected in amounts as high as 1.2% (wt/wt) of the total fatty acids. Accompanying the occurrence of gamma-linolenic acid in transgenic somatic soybean embryos was an unidentified compound with a retention time intermediate to that of methyl α-linolenic acid ($18:3\Delta^{9,12,15}$) and methyl eicosanoic acid (20:0) on a polar GC column, such as Omegawax 320 (Supelco). Analysis by GC-MS indicated that this compound had an apparent molecular ion of 294 m/z. This compound accounted for . . . 0.5% of the total fatty acids of individual embryos from transformation event MS 151-5-4 and was only found in embryos that contained detectable amounts of gamma-linolenic acid. Overall, the presence of gamma-linolenic acid in transgenic somatic soybean embryos confirms that the introduced gene is capable of enhancing a A6 desaturation event in a tissue that normally does not accumulate fatty acids with these bonds. The production of tariric acid by this enzyme cannot be addressed due to the low overall accumulation of $A^6$ containing fatty acids. Isolation of embryos expressing higher levels of the introduced gene may resolve this question.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide that encodes a plant sphingolipid desaturase polypeptide having a sequence identity of at least 80%, based on the Clustal method of alignment, when compared to a polypeptide selected from the group consisting of SEQ ID NOs: 2, 4, and 8.

2. The polynucleotide of claim 1 wherein the sequence identity is at least 85%.

3. The polynucleotide of claim 1 wherein the sequence identity is at least 90%.

4. The polynucleotide of claim 1 wherein the sequence identity is at least 95%.

5. The polynucleotide of claim 1 wherein the polypeptide is selected from the group consisting of SEQ ID Nos:2, 4, and 8.

6. The polynucleotide of claim 1, wherein the polynucleotide is selected from SEQ ID Nos:1, 3, and 7.

7. An isolated complement of the polynucleotide of claim 1, wherein (a) the complement and the polynucleotide consist of the same number of nucleotides, and (b) the nucleotide sequences of the complement and the polynucleotide have 100% complementarity.

8. An isolated sphingolipid desaturase polypeptide having a sequence selected from the group consisting of SEQ ID NOs: 2, 4, and 8.

9. A recombinant DNA construct comprising the polynucleotide of claim 1 operably linked to at least one regulatory sequence.

10. The recombinant DNA construct of claim 9, wherein the recombinant DNA construct is an expression vector.

11. A method for altering the level of plant sphingolipid desaturase polypeptide expression in a host cell, the method comprising:

(a) transforming a host cell with the recombinant DNA construct of claim 9; and (b) growing the transformed cell in step (a) under conditions suitable for the expression of the recombinant DNA construct.

12. A method for transforming a cell comprising introducing into a cell the recombinant DNA construct of claim 9.

13. A method for producing a transgenic plant comprising (a) transforming a plant cell with the recombinant DNA construct of claim 9, and (b) regenerating a plant from the transformed plant cell.

14. A method for producing gamma linolenic acid in soybean plants, the method comprising (a) transforming a soybean cell with the recombinant DNA construct of claim 9, and (b) regenerating transgenic plants from the transformed cell of (a), wherein plants comprising the recombinant DNA construct of claim 9 produce gamma linolenic acid which is normally not produced in soybean plants.

15. The polynucleotide of claim 1 wherein the sphingolipid desaturase is a delta-6-desaturase.

16. A transgenic cell comprising the recombinant DNA construct of claim 9.

17. The cell of claim 16, wherein the cell is selected from the group consisting of a yeast cell, a bacterial cell, an insect cell, and a plant cell.

* * * * *